United States Patent
Mech et al.

(10) Patent No.: US 12,329,974 B2
(45) Date of Patent: Jun. 17, 2025

(54) PHOTOPLETHYSMOGRAPHY IN COMBINATION WITH MEDICAL DEVICES

(71) Applicant: The Alfred E. Mann Foundation for Scientific Research, Valencia, CA (US)

(72) Inventors: Brian Mech, Buffalo, MN (US); Robert Greenberg, Los Angeles, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

(21) Appl. No.: 17/692,761

(22) Filed: Mar. 11, 2022

(65) Prior Publication Data
US 2022/0288398 A1    Sep. 15, 2022

Related U.S. Application Data

(60) Provisional application No. 63/159,840, filed on Mar. 11, 2021.

(51) Int. Cl.
*A61N 1/36* (2006.01)
*A61N 1/362* (2006.01)
*A61N 1/365* (2006.01)

(52) U.S. Cl.
CPC ..... *A61N 1/36585* (2013.01); *A61N 1/36031* (2017.08); *A61N 1/3606* (2013.01);
(Continued)

(58) Field of Classification Search
CPC ............. A61B 5/02416; A61B 5/0261; A61B 5/14551; A61B 5/4806; A61B 5/4836;
(Continued)

(56) References Cited

U.S. PATENT DOCUMENTS

| | | | |
|---|---|---|---|
| 6,006,134 A * | 12/1999 | Hill | A61B 17/3417 607/9 |
| 7,469,697 B2 * | 12/2008 | Lee | A61M 16/024 607/9 |
| 8,649,865 B2 * | 2/2014 | Bornzin | A61N 1/3686 607/18 |
| 2005/0115561 A1 | 6/2005 | Stahmann et al. | |

(Continued)

FOREIGN PATENT DOCUMENTS

| | | |
|---|---|---|
| RU | 2657966 C2 | 6/2018 |
| WO | 2018/102599 A1 | 6/2018 |
| WO | 2020/092701 A2 | 5/2020 |

OTHER PUBLICATIONS

International Search Report and Written Opinion issued for Int'l Appl. No. PCT/US2022/071107, Int'l Filing Date Mar. 11, 2022, mailed Jun. 8, 2022.
(Continued)

*Primary Examiner* — Amanda K Hulbert
(74) *Attorney, Agent, or Firm* — ARENTFOX SCHIFF LLP (57) ABSTRACT

The disclosure provides systems and methods for detecting, monitoring, and/or treating obstructive sleep apnea, as well as other conditions, using vital sign and/or biometric data collected and/or imputed from one or more photoplethysmography sensors in conjunction with vital sign and/or biometric data from one or more additional sensors such as activity, body position, ECG, HR, or $SpO_2$ levels, e.g., as feedback to control therapy and/or to titrate therapy on a periodic basis.

20 Claims, 6 Drawing Sheets

(52) U.S. Cl.
CPC ..... *A61N 1/36139* (2013.01); *A61N 1/36171* (2013.01); *A61N 1/36175* (2013.01); *A61N 1/36178* (2013.01); *A61N 1/36192* (2013.01); *A61N 1/3625* (2013.01); *A61N 1/3627* (2013.01)

(58) Field of Classification Search
CPC .......... A61M 16/024; A61M 2230/005; A61M 2230/04; A61M 2230/06; A61M 2230/205; A61M 2230/30; A61M 2230/40; A61M 2230/63; A61M 5/142; A61M 5/1723; A61N 1/36031; A61N 1/3606; A61N 1/36139; A61N 1/36171; A61N 1/36175; A61N 1/36178; A61N 1/36192; A61N 1/3625; A61N 1/3627; A61N 1/36514; A61N 1/36585
See application file for complete search history.

(56) References Cited

U.S. PATENT DOCUMENTS

| | | | |
|---|---|---|---|
| 2007/0173728 A1 | 7/2007 | Pu et al. | |
| 2011/0124979 A1* | 5/2011 | Heneghan | A61B 5/346 600/301 |
| 2018/0185643 A1 | 7/2018 | Lee et al. | |
| 2020/0337563 A1 | 10/2020 | Andersen | |
| 2020/0360696 A1 | 11/2020 | Pikov et al. | |
| 2022/0134102 A1* | 5/2022 | O'Connor | H02J 50/20 607/42 |

OTHER PUBLICATIONS

European Search Report received for Patent Application No. 22768233.3, mailed on Mar. 12, 2025, 7 pages.

* cited by examiner

PHOTOPLETHYSMOGRAPHY IN COMBINATION WITH MEDICAL DEVICES

CROSS-REFERENCE TO RELATED APPLICATION

This application claims the benefit of U.S. Provisional Application Ser. No. 63/159,840, entitled "PHOTOPLETHYSMOGRAPHY IN COMBINATION WITH MEDICAL DEVICES," which was filed on Mar. 11, 2021, and is expressly incorporated by reference herein in its entirety.

BACKGROUND

Medical devices deliver therapy to patients suffering from a wide variety of conditions and illnesses. Increasingly, there is a desire to modulate the therapeutic delivery in response to the condition of the patient, which often varies over the course of a day, and nearly always varies over the course of weeks, months, and years. Many such devices are adjusted periodically by patients or physicians during an office visit when new data is collected from diagnostic tests that might be run. For example, a cardiac rhythm management (CRM) device might be adjusted based on an ECG result. In some cases, sensors have been incorporated into wearable devices which provide more immediate results. Such devices include, e.g., a heart rate detector for an atrial defibrillator that can trigger stimulus when fibrillation is detected, a glucose test for a diabetic that then results in adjustment of insulin delivery, and a blood oxygen saturation sensor that can alert a patient as to a respiratory issue. The increased use of diagnostic devices, both in a clinical setting and in consumer-focused wearable devices, has begun to revolutionize healthcare.

Relatively recently, photoplethysmography (PPG) has emerged as an increasingly popular technology that can directly measure or impute from infrared measurement of blood volume changes in several patient-related biomarkers (e.g., vital signs, molecular/physiological markers, or biometric parameters). PPG refers to acquiring a volumetric organ measurement by optical means. Frequently, pulse oximeters are employed, which detect changes in light absorption properties of the human skin. Typically, a transmissive or reflective blood PPG sensor monitors the perfusion of blood to the dermis and subcutaneous tissue of the skin through absorption measurement at a specific wavelength. Besides light originating from blood, there is a far greater portion of light detected, which originates from tissue and ambient light, which must be taken into account when analyzing PPG-derived data.

Conventional medical devices for monitoring biomarkers typically include only a single sensor (e.g., a PPG sensor), or a plurality of sensors wherein each sensor provides a separate output. A physician may choose to take into account the output from a plurality of sensors. However, limited options are available with respect to medical devices that can effectively leverage sensor data provided by a plurality of sensors.

BRIEF SUMMARY OF EXEMPLARY ASPECTS OF THE DISCLOSURE

In view of the foregoing and other deficiencies associated with conventional medical devices, the present disclosure provides systems and methods that can be implemented in connection with medical devices for monitoring wide variety of conditions and illnesses and/or for modulating treatment. Medical devices based on this disclosure can be used to improve patient care and outcomes, as well as for more efficient allocation of medical resources (e.g., by encouraging the selection and application of effective treatments).

In some aspects, a medical device according to the disclosure may comprise at least one PPG sensor, alone or in combination with one or more additional sensors, wherein each sensor is configured to detect, determine, measure, and/or monitor at least one biomarker parameter of a human subject (e.g., vital signs, molecular/physiological markers, or biometric parameters). Each sensor may be configured to obtain data from the subject on command, periodically, or continuously (e.g., based on a predetermined sampling rate, which may be adjusted as described below). As used herein, a system comprising a PPG sensor and one or more additional sensors configured to detect and/or monitor at least one vital sign or biometric parameter of a human subject is interchangeably referred to as a "PPG Sensor System" or "PPGSS."

The PPG sensor may be configured to detect, measure, and/or monitor: blood oxygen saturation, heart rate, respiration rate, stroke volume, cardiac output, pulse pressure, systemic vascular resistance, arterial pressure, cardiac index, and/or others biomarkers (e.g., vital signs, molecular/physiological markers, or biometric parameters).

Each of the additional sensors used in a PPGSS may be configured, e.g., to detect, measure, and/or monitor one or more of the following biomarkers: body temperature; activity and/or body position (e.g., through the use of an accelerometer/motion detection); the presence or level of sweat on the skin; a signal from a single-electrode or low electrode count ECG; pupil size changes; the occurrence or quantity of seizures; the level of glucose, insulin, noradrenaline, norepinephrine, acetylcholine, dopamine, cortisol, serotonin, and/or glutamate; an EEG; an EMG; heart rate variability; or MSNA (muscle sympathetic nerve activity); of a human subject.

These sensors used by the PPG/PPGSS may be configured to detect, measure, and/or monitor the existence of any of the biomarkers described herein (e.g., the occurrence of a seizure, or a change in pupil size), the quantity of any of the biomarkers described herein (e.g., a level of glucose or dopamine, or a number of seizure experienced by the human subject), and changes over time or as compared to historic or periodically-collected data points. For example, in some aspects the PPG/PPGSS may be configured to detect a change in the absolute or relative level of any biomarker described herein, as compared to a previously recorded level or a historic level.

In some aspects, the PPG/PPGSS may be configured to activate, cease, increase, decrease, and/or titrate a therapy (e.g., the administration of stimulation or of an active agent) provided by a treatment device, when the quantity, level, or concentration of one or more of the biomarkers described herein increase or decreases, or if a state change is detected (e.g., a change in activity or body position). In some aspects, the PPG/PPGSS may be configured to activate, adjust, cease, increase, decrease, and/or titrate a therapy when the quantity, level, or concentration of one or more of the biomarkers described herein increases or decreases by at least, exactly, or about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100%, or by an amount within a range with endpoints defined by any of the foregoing integer values. For example, the PPG/PPGSS may be configured to increase the level of a treatment provided by a treatment device for sleep apnea if the subject's $SpO_2$ level decreases by more than 5%. The change in the quantity, level, or concentration of one or more of the biomarkers may be measured as compared to: a) a baseline value; b) a last detected/measured value recorded for the subject; c) a historical value recorded for the subject (e.g., a value recorded at least, exactly, or about 1, 2, 3, 4, 5, 6, 7, 8, 9, 10, 15, 20, 25, 30, 35, 40, 45, 50, 55, or 60 minutes ago, or within a range defined by any of these time points); d) an average value for a healthy human subject (e.g., who does not have the medical condition for which the subject is receiving treatment); ore) a value recognized in the art as a standard level for a human subject (e.g., for an adult male, an adult female, or an adolescent).

Similarly, the PPG/PPGSS may be configured to adjust, cease, increase, decrease, and/or titrate a therapy in response to specific state changes (e.g., in the body position or activity of the subject) within a predefined period of time or if a constant state is detected for a minimum amount of time subject (e.g., for at least or within exactly or about 1, 2, 3, 4, 5, 6, 7, 8, 9, 10, 15, 20, 25, 30, 35, 40, 45, 50, 55, or 60 minutes). For example, the PPG/PPGSS may be configured to switch to a mode wherein a treatment is administered according to a specific level of intensity or schedule when a subject is detected as being asleep or laying in a supine/prone/side position for a preset amount of time, and a different mode when the subject is detected as standing, sitting or otherwise engaging in activities associated with being awake.

As noted above, the PPG/PPGSS may be configured to detect, measure, and/or monitor the activity and/or body position of the subject. Activities may include a set of one or more predefined activities (e.g., whether the subject is sleeping, walking, running, swimming), or activities classified based on a level of exertion (e.g., low-, medium- or high-intensity activity). The body position of the subject may be determined to be, e.g., standing, sitting, prone, supine, or laying on a side. In some aspects, the PPG/PPGSS may be configured to detect, measure, or monitor state changes regarding the activity and/or body position of the subject, e.g., over a period of time. For example, the PPG/PPGSS may be configured to detect that a subject is asleep (or that the subject has been asleep for a period of time above a preset threshold) based upon the body position or other biomarker data, e.g., and may activate (or adjust the level of) a treatment provided by a treatment device in response.

Medical devices that leverage biomarker parameters obtained from a PPG sensor data, in combination with biomarker parameters obtained from one or more additional sensors, can be used to determine other measures of human health that may not otherwise be accurately determined when a single sensor is used (e.g., blood pressure and sleep disordered breathing events). By utilizing multiple data sources, medical devices according to the disclosure may be used to detect and/or monitor diseases and medical conditions, and optionally, to guide treatment (by controlling and/or titrating a therapy delivered by a cardiac device, sleep apnea device, etc.).

The following presents a simplified summary of several exemplary embodiments in order to provide a basic understanding of the inventions described herein. This summary is not intended as an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In a first general aspect, the disclosure provides a system for delivering therapy to treat a medical condition of a human subject, comprising: a photoplethysmography (PPG) sensor configured to detect and/or monitor a first biomarker parameter of the subject; and a treatment device configured to administer a therapeutic treatment or stimulation to the human subject; wherein the treatment device is controlled based on the first biomarker parameter.

In some aspects, the first biomarker parameter comprises one or more of: an oxygen saturation level, a heart rate, a respiration rate, a stroke volume, a cardiac output, a pulse pressure, a systemic vascular resistance, an arterial pressure, or a cardiac index, of the human subject.

In some aspects, the system further comprises at least one additional sensor configured to detect and/or monitor a second biomarker parameter of the subject.

In some aspects, the second biomarker parameter comprises one or more of: a body temperature, an activity and/or body position, a presence or level of sweat on the skin, or a single-electrode or low ECG, of the human subject.

In some aspects, the treatment device is further controlled based on the second biomarker parameter.

In some aspects, the treatment device is configured to administer, cease administering, titrate, or adjust the level of a treatment or stimulation administered to the human subject, based on the first biomarker parameter, the second biomarker parameter, or a combination thereof.

In some aspects, the treatment device is a medical device implanted in the subject.

In some aspects, the treatment device is a stimulation device.

In some aspects, the treatment device is an external stimulation device.

In some aspects, the treatment device is configured to stimulate the human subject's heart.

In some aspects, the treatment device is configured to stimulate: a) at least one nerve of the human subject, optionally one or more of a vagus, phrenic, sacral, tibial, hypoglossal, pharyngeal, glossopharyngeal, occipital, spinal, cranial, cavernous, facial, radial, ulnar, auditory, esophageal, laryngeal, femoral, frontal, cardiac, cervical, hypogastric, plantar, mandibular, perineal, pelvic, saphenous, splanchnic, splenic, tympanic, renal, thoracic, vestibular or trigeminal nerve of the human subject, or any of their branches; and/or b) at least one tissue or organ of the human subject, optionally one or more of the heart, carotid sinus, vocal cords, tongue, or muscles, of the human subject.

In some aspects, the treatment device is configured to stimulate at least one nerve associated with upper airway patency.

In some aspects, the treatment device is configured to stimulate the hypoglossal nerve and/or the phrenic nerve of the human subject.

In some aspects, the first biomarker parameter comprises data based on apnea and hypopnea events, the rate thereof, or an apnea hypopnea index (AHI).

In some aspects, the first biomarker parameter and/or the second biomarker parameter comprise data based on apnea and hypopnea events, the rate thereof, or an apnea hypopnea index (AHI).

In some aspects, the treatment device is configured to: a) provide electrical stimulation; and b) adjust one or more parameters of the electrical stimulation based on the first biomarker parameter, wherein adjustment comprises modulation of the amplitude, frequency, pulse width, duty cycle, or bursting parameters of the electrical stimulation.

In some aspects, the treatment device is configured to: a) provide electrical stimulation to at least one nerve associated with upper airway patency; and b) adjust one or more parameters of the electrical stimulation based on the first biomarker parameter and/or the second biomarker parameter, wherein adjustment comprises modulation of the amplitude, frequency, pulse width, duty cycle, or bursting parameters of the electrical stimulation.

In a second general embodiment, the disclosure provides a method for delivering therapy to treat a medical condition of a human subject, comprising: detecting and/or monitoring, by a photoplethysmography (PPG) sensor, a first biomarker parameter of the subject; optionally, detecting and/or monitoring, by at least one additional sensor, a second biomarker parameter of the subject; and controlling a treatment device configured to administer a therapeutic treatment or stimulation to the human subject based on the first biomarker parameter, and optionally, the second biomarker parameter.

In some aspects, the medical condition treated by the systems and methods described herein comprises: sleep apnea, hypertension, and/or an abnormal heart rhythm/rate. In some aspects, the medical condition treated by the systems and methods described herein comprises: epilepsy, depression, heart failure, an autoimmune disease, a systemic inflammatory disease, diabetes, obesity, and/or chronic pain.

In some aspects, the treatment device comprises: an implantable pulse generator connected to one or more electrodes (e.g., for applying stimulation to one or more nerves as a treatment for sleep apnea or any other condition described herein), a pacemaker (e.g., for the treatment of arrhythmia), a pump (e.g., configured to deliver a therapeutic agent to the human subject), a stent, or any other device configured to apply to apply therapeutic stimulation or a therapeutic agent to a human subject.

In a third general embodiment, the disclosure provides a method for delivering therapy to treat a medical condition of a human subject (e.g., sleep apnea, hypertension, an abnormal heart rhythm/rate) using any of the systems described herein.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

As explained in further detail herein, systems and methods according to the present disclosure may be used to detect, monitor, and/or treat various medical conditions based on biomarker parameters obtained from a PPG or a PPGSS. PPG alone or in combination with other basic sensors, can be used to monitor more than 14 vital signs, providing applications useful for both hospital and at-home patient monitoring, as well as in consumer wellness and fitness products. As data is collected from PPG devices over time, other biomarker parameters can be imputed from standard PPG signals, e.g., using the power of machine learning and/or artificial intelligence. PPG data and any biomarker parameters derived therefrom can further be combined with biomarker parameters detected and/or monitored using other sensors (e.g., an accelerometer, thermometer, gyroscope, etc.). In many cases, the combined data stream results in more accurate or otherwise improved treatment of various medical conditions (e.g., sleep apnea). The systems described herein utilize data from a PPG sensor, alone or in combination with data from one or more additional sensors, to control a therapeutic device (a stimulator, pump, stent, etc.). Control in this context may comprise starting, ending, titrating, or adjusting a therapy (e.g., electrical or other stimulation, or the administration of a therapeutic agent).

In some aspects, the PPG sensor, and/or the optional additional sensor(s) may be incorporated into a wearable device such as a smart watch or other wrist-worn device, a patch, or any other form factor. Biomarker parameters may be obtained directly or imputed based on a signal that is directly detected or measured. Wearable embodiments provide a means for the detection and/or measurement of biomarker parameters that are otherwise difficult to collect or difficult to collect on a continuous basis, in a daily life setting. Accordingly, such embodiments are advantageous in that they provide greater access to data and also typically improve compliance (e.g., subject may be more inclined to utilize wearable devices on a regular basis).

Data collected from a PPG or PPGSS may be used to inform a patient, caregiver or physician regarding therapeutic effectiveness, or to control therapy by acting as feedback. For example, data collected from a PPGSS may confirm that a stimulation regimen is adequate to prevent or reduce disordered sleep, or may alternatively show that a current regimen is ineffective, prompting a physician to adjust the parameters of the therapy. In some embodiments, the PPG or PPGSS may communicate with the treatment device directly in order to adjust or otherwise modify a treatment. For example, a PPGSS may detect and/or measure one or more biomarker parameters which indicate that a subject requires increased administration of a therapeutic agent, and communicate wirelessly with a pump to activate or increase administration of the therapeutic agent). As another example, a PPG may be used to measure apnea and hypopnea and may be configured to communicate with a device intended to treat sleep disordered breathing to identify when it is occurring and what the severity is, allowing for proper therapeutic intervention (e.g., via electrical stimulation provided by an implanted pulse generator), or to adjust the degree of a therapy being delivered (e.g., the amplitude, frequency, pulse width, duty cycle, or bursting parameters of electrical stimulation provided by an implanted pulse generator).

In some aspects, biomarker parameter data collected using a PPG or PPGSS may be used to identify or treat other medical conditions or co-morbidities. For example, biomarker parameters obtained from a PPG or PPGSS may be used to accurately determine blood pressure in a comfortable to use continuous ambulatory format, which can be used, among other things, to adjust therapies intended to treat hypertension.

In some aspects, PPG and PPGSS-based medical devices according to the disclosure may utilize intra- and/or inter-patient data that are collected longitudinally over time and analyzed using machine learning and/or artificial intelligence, in order to evaluate the biomarker parameters obtained from a human subject, and/or to guide or direct treatment of the human subject.

PPG and PPGSS for Treatment of Cardiac Diseases and Disorders

Figure 1:
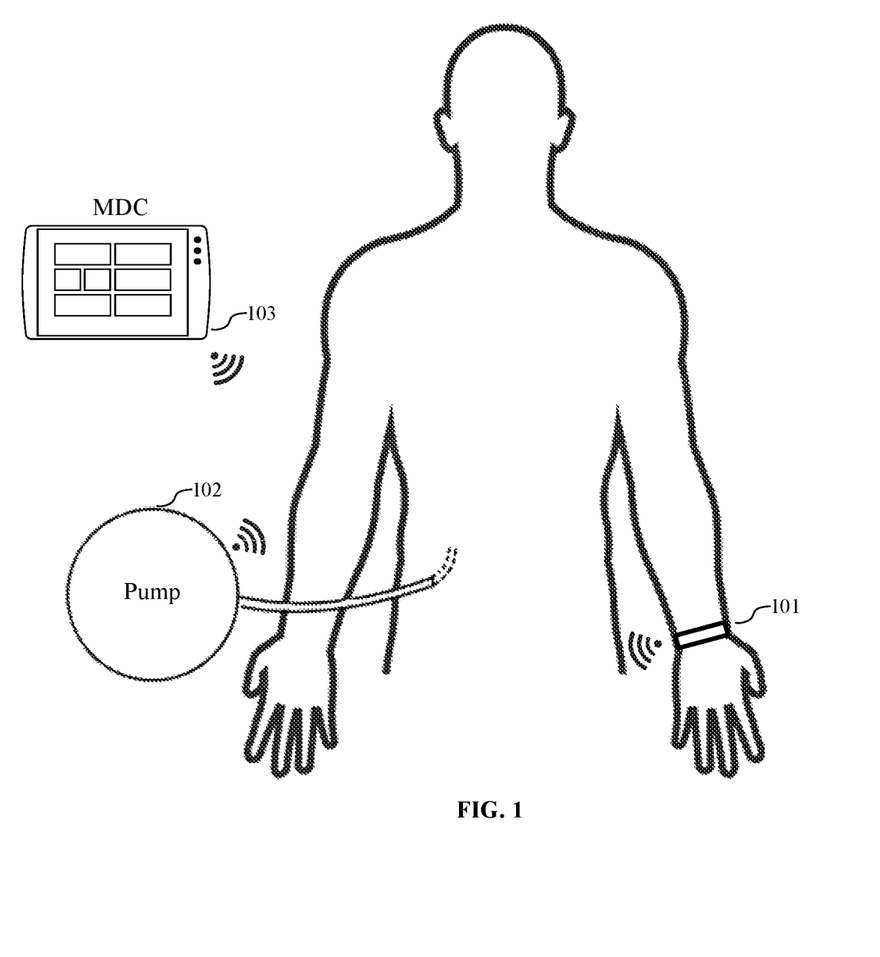
FIG. 1 is a diagram illustrating an exemplary embodiment of a system for controlling a therapy using a PPGSS. As described in further detail below, this figure depicts two potential configurations of such a system.

FIG. 1 is a diagram illustrating an exemplary embodiment of a system 100 for controlling a therapy using a PPGSS configured to collect cardiac and/or hemodynamic data. As described in further detail below, this figure depicts two potential configurations, wherein a treatment device (in this case pump 102) is controlled based on biomarker parameters obtained from a wearable device 101 comprising a PPG sensor and at least one additional sensor (e.g., an accelerometer, gyroscope, $SpO_2$ sensor, ECG sensor, or heart rate sensor).

Data collected and/or imputed from one or more PPG sensors can provide cardiac and/or hemodynamic biomarker parameter data that can be used, in conjunction with biomarker parameter data obtained from one or more additional sensors (e.g., activity, body position, ECG, heart rate, blood pressure, $SpO_2$), or alone, as feedback to control a therapy delivered by cardiac devices and/or to titrate therapy on a periodic basis. PPG sensing may be used to predict the onset of acute events and to control delivery of therapy through cardiac devices (e.g., modified electrical stimulation administered via an implanted pacemaker) to prevent or minimize the impact of such events. PPG-derived biomarker parameter data may also be used to control the delivery of an additional therapeutic agent such as a drug, or a biologic, e.g., by alerting and/or directing a health care provider or a patient to administer the therapeutic agent. In some aspects, the present systems may be comprise a PPG or PPGSS configured to communicate with a treatment device such as a pump 102, a stimulator, or other device capable of administering a treatment to the human subject.

In some aspects, the treatment device comprises a cardiac rhythm management (CRM) device, including without limitation pacemakers and defibrillators, heart failure devices including vagus nerve stimulators, baroreflex stimulators, artificial hearts, left ventricular assist devices (LVADS), bi-ventricular assist devices (BiVAD), and others cardiac-related devices. In some aspects, the biomarker parameters comprise feedback provided on a continuous basis, periodically, or manually upon activation by a user, a physician, or a third-party. In some aspects, the treatment device is a stent, or any other vascular support device, e.g., capable or adjusting its size and/or controlling the rate at which drug is eluted, or some other functional aspect, basedon on hemodynamic and/or cardiac feedback.

As illustrated by FIG. 1, a PPG or PPGSS may be configured to communicate directly with a treatment device or via an intermediate device. Each sensor may configured to communicate via a wired or wireless connection. For example, in FIG. 1 the PPG sensor and at least one additional sensor are housed in a wearable device 101 that incorporates a wireless communication system. In this example, the wireless device 101 is configured to communicate directly with a treatment device (in this example, the pump 102) and/or with an intermediate monitor/display/controller (MDC) device 103. The MDC device 103 comprises an electronic device (e.g., a computer, tablet, or laptop) configured to monitor and display at least one biomarker parameter obtained directly from or imputed from sensor data collected by the PPG and/or PPGSS (e.g., blood pressure, heart rate, or $SpO_2$). The MDC device 103 may be further configured to control at least one treatment device capable of controlling the administration of a treatment to the human subject being evaluated by the PPG or PPGSS (e.g., the level of stimulation or amount of an active agent administered to the subject). In this example, the MDC 103 is configured to control the flow rate of the pump 102 in response to biomarker parameters detected and/or measured by the PPGSS housed in the wireless device 101. In some aspects, the MDC 103 may comprise an alert system configured to provide a visual and/or audible alert when one or more of the biomarker parameters detected and/or measured by the PPGSS is outside of a predetermined range. In some aspects, the MDC 103 is configured to communicate with the treatment device and/or the PPG/PPGSS via a local wireless network, via a cloud-based connection, or via any other means of wireless or wired communication known in the art. In many aspects, the PPG/PPGSS, MDC 103 and/or the treatment device will be configured for bi-directional communication.

It is expressly understood that any functional aspects of the MDC 103 may be integrated into the PPG or PPGSS, in whole or in part. For example, in some aspects the PPG or PPGSS is housed in a wireless device 101 that includes a display capable of displaying one or more biomarker parameters detected and/or measured by the PPG or PPGSS sensors, and memory capable of storing historical biomarker parameter data (e.g., allowing the device to monitor such parameters). The PPG or PPGSS may also be configured to execute software code (e.g., decisional logic, and/or artificial intelligence or machine learning based processing) in order to evaluate the biomarker parameter data obtained from the PPG and PPGSS and to control operation of the treatment device. Control may comprise activation, reduction, cessation, titration, or adjustment of the treatment provided by the treatment device (a level or timing of stimulation, a rate or amount of active agent administered by the treatment device, etc.). In this example, all of the functionality of the MDC 103 is performed by the PPG/PPGSS. In other embodiments, functionality may be split between the PPG/PPGSS and the MDC 103 (e.g., the MDC 103 may be configured to apply more energy-intensive processing of the biomarker parameter data, or to store long term historical biomarker parameter data).

PPG and PPGSS for Treatment of Hypertension

Hypertension is a major health concern for adults. Chronic hypertension can lead to several life-threatening conditions. Hypertension is typically treated with oral medication, but can also be treated by other means, including intravenous medication, and neuromodulation. Ideally, blood pressure should be monitored continuously, or periodically, to inform the dose of any therapy. Practically, this has proven to be very difficult because the standard device used to monitor blood pressure, a sphygmomanometer, is bulky and uncomfortable and not something that the average person can or will use for continuous monitoring. In contrast, the PPGSS described herein may be configured as a small wearable device (e.g., as a wrist-mounted device like a watch, as a patch-like device that can be placed on the chest, or in other easy to wear form factors). Thus, PPGSS-based devices provide a simple and discrete means for continuous or periodic monitoring of a subject's hypertensive state (blood pressure) that can be used to guide treatment decisions.

In some aspects, a PPGSS may be configured to generate audible or visual alerts for the subject, or for a caregiver or physician, in real time or during a post hoc analysis of the biomarker data generated by the PPGSS. In some aspects, the PPGSS may be configured to inform a patient, caregiver, and/or physician of their blood pressure over the course of a day, or when an additional bolus of therapy may be required. In some aspects, the PPGSS may be configured to provide feedback control for a therapy, e.g., an electrical stimulation therapy, oral therapy, intravenous therapy, therapy delivered by a pump, or any other hypertensive therapy. Feedback control may entail changes to dosage of a treatment, including stimulation parameters (voltage, amplitude, frequency, pulse width, duty cycle, bursting parameters, etc.), a number or amount of pills or oral medication administered to the subject, or a frequency of consumption or delivery rate of a drug (e.g., in a liquid or aerosol form) to the subject. In some aspects, e.g., the intensity (or any other parameter) of a treatment or treatment device may be increased or decreased by at least, exactly, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100%, or by an amount within a range with endpoints defined by any of the foregoing integer values, in response to feedback obtained from the PPG/PPGSS.

In some aspects, the PPGSS may be configured to communicate with the treatment device, the subject, a caregiver, or a physician responsible for delivering the therapy, in real time, or periodically. Communication may take place via a wired, wireless, and/or cloud-based interface.

In some aspects, the PPGSS may be configured to collect blood pressure (BP) data continuously and to save it on a storage medium. The PPGSS may further be configured to periodically connect to a computing device such as a mobile phone or computer, that can connect with a cloud-based device to upload that data for analysis by a third party (e.g., a physician). For example, a physician may be required to approve of a change in hypertensive therapy based on the biomarker parameters generated by the PPGSS, and to communicate approval back to the subject. In some aspects, the PPGSS and/or the treatment device maybe configured to receive approval from a third party (e.g., a physician) before changing one or more treatment parameters. Communication may take place via any of the means of communication described herein.

As indicated elsewhere in this disclosure, any functionality provided by the PPGSS may alternatively be offloaded to an MDC 103. Such embodiments were described above in the context of systems for treating cardiac diseases and disordered. However, to be clear this configuration may be used with systems designed to treat hypertension or any of the other applications described herein. Furthermore, while the use of PPGSS in the treatment of hypertension is described above, it should also be understood that similar use is applicable to pulmonary arterial hypertension (PAH) and any hemodynamic or blood-related disease as well.

Detection of Comorbidities Using PPG and PPGSS

Since a PPG or PPGSS can detect, measure and impute various biomarker parameters, it should be appreciated that a PPG/PPGSS may also be used to detect illnesses generally, and conditions that are comorbid with the primary condition(s) being treated when a device or medication, or more broadly any therapy, is being used to treat a primary condition. Thus, PPG or PPGSS-based monitoring may be used to detect other health conditions, either prevailing or as they arise. Similar, the biomarker parameter data obtained by the PPG/PPGSS maybe comprise information that allows a healthcare professional to determine that other conditions are prevailing or have arisen.

Figure 2:
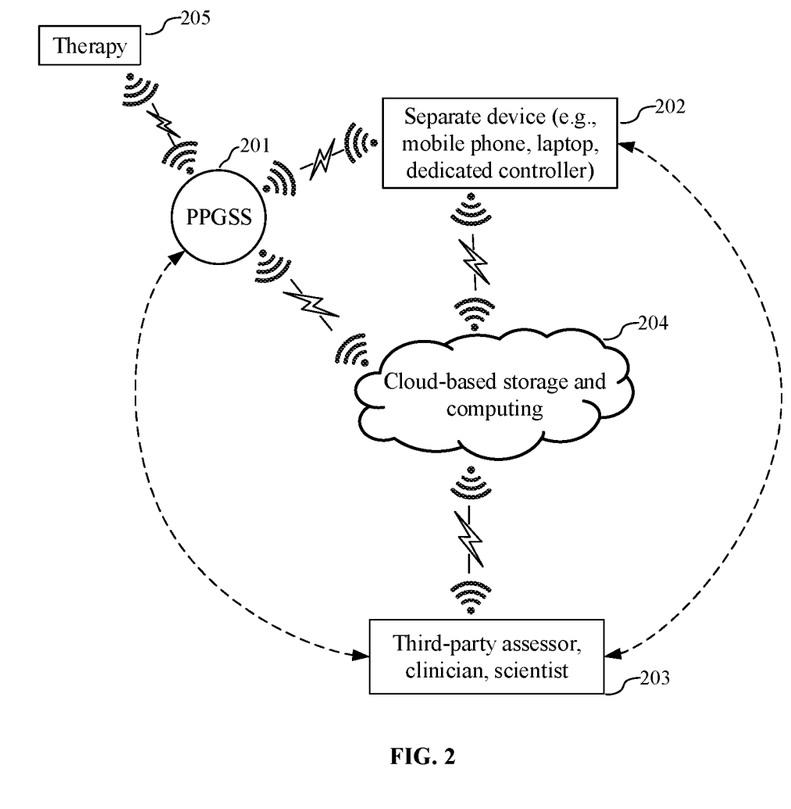
FIG. 2 is a diagram illustrating an exemplary embodiment of a system wherein a PPGSS is used to control a therapy (e.g., by directly connecting to a therapeutic device or by providing guidance to a treatment provider), in addition to being in communication with a third-party service capable of analyzing data provided by the PPGSS (e.g., by direct communication or via a cloud-based infrastructure).

FIG. 2 is a diagram illustrating an exemplary embodiment of a system wherein a PPGSS is used to control a therapy (e.g., by directly connecting to a therapeutic device or by providing guidance to a treatment provider), in addition to being in communication with a third-party service capable of analyzing data provided by the PPGSS (e.g., by direct communication or via a cloud-based infrastructure).

A therapeutic system according to FIG. 2 may possess communication capabilities according to any of the embodiments described herein, allowing biomarker parameter data collected by the PPG/PPGSS, and/or the treatment device to be delivered to a subject being treated, a caregiver or physician, to the cloud, via the cloud to remote third parties, or directly to remote third parties (via a means other than the cloud). In turn, the PPG/PPGSS and/or the treatment device may be configured to receive data, including instructions to adjust a therapy, or a diagnosis, or a potential diagnosis from a local or remote third party (e.g., a physician). In some aspects, the instructions, diagnosis, or potential diagnosis may be generated by an artificial intelligence or machine learning algorithm(s) located in the cloud, or on the edge of the therapeutic system, or another system in the possession of the local or remote third parties.

This ability to diagnose new or prevailing conditions, or potential new or prevailing conditions, enables improved health outcomes for patients who might be alerted to go see a primary care physician, or a specialist, or have a telemedicine appointment with an appropriate healthcare professional (HCP) recommended/scheduled. For example, a local or remote third party may be an HCP who can recommend a new therapy, a new adjunctive therapy, or possibly change the therapy being delivered by the therapeutic system to treat or alleviate the new diagnosis (e.g., in cases where the therapeutic system is potentially delivering a therapy that causes the co-morbidity).

In brief, as illustrated by FIG. 2 a PPG/PPGSS 201 may be configured to communicate with a separate device 202 (e.g., a mobile phone, laptop, dedicated controller such as an MDC device), and with a third-party assessor, clinician, or scientist 203 (e.g., an HCP). Communication may take place directly or via an intervening cloud-based storage and computing 204 infrastructure. The PPG/PPGSS 201 may also be configured to communicate with the means for treatment 205 (e.g., a treatment device as described herein). In some cases, treatment may be provided by the subject, a caregiver, a physician, etc. As such, it is understood that the PPG/PPGSS 201 may alternatively communicate with the means for treatment 205 via a visual interface, via audible alerts/instructions, etc. (not shown in FIG. 2).

PPG and PPGSS for Treatment of Sleep Apnea

Figure 3:
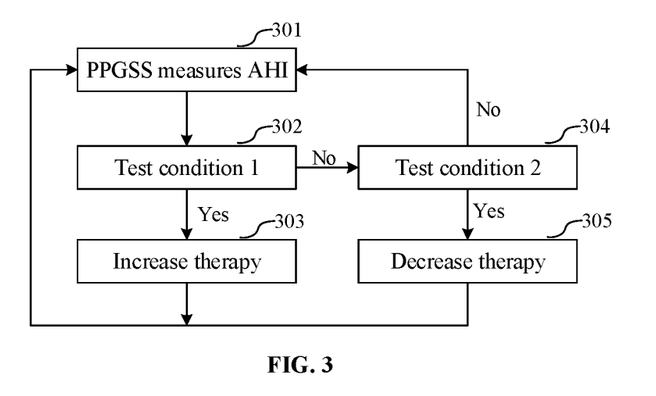
FIG. 3 is a flowchart illustrating aspects of an exemplary embodiment of a control algorithm for sleep-disordered breathing using a PPG or PPGSS device.
Figure 4:
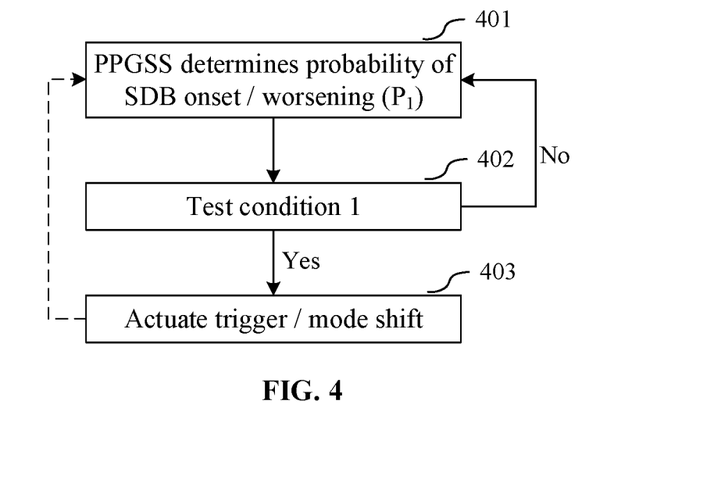
FIG. 4 is a flowchart illustrating aspects of an exemplary embodiment of a PPGSS-based probability determination to trigger therapy or heightened system readiness (e.g., for sleep-disordered breathing).

FIG. 3 and FIG. 4 depict flowcharts illustrating aspects of an exemplary embodiment of a control algorithm for sleep-disordered breathing using a PPG or PPGSS device.

A PPG/PPGSS-based medical device may be used to replicate all or some of the functionality of a polysomnography (PSG) study, which is typically used to diagnose sleep-disordered breathing. Thus, it may offer a smaller, simpler, and less expensive way to conduct sleep studies in a sleep clinic or at home, or at least to identify the magnitude of sleep-disordered breathing. The PPG/PPGSS approach also offers a viable means for monitoring sleep and sleep-disordered breathing on a nightly basis, either continuously or periodically. Notably, the ability of a system that includes PPG/PPGSS may be configured to identify apnea and hypopnea events. The detection of these events could be used to control treatment devices intended to treat sleep apnea including CPAP/VPAP/BPAP devices, negative pressure devices, tongue stimulators, hypoglossal nerve stimulators, phrenic nerve stimulators, and other devices designed to stimulate nerves and/or muscles associated with upper airway patency and/or respiration. The detection of these events by a PPG or PPGS S, either in isolation, or alongside detection of sleep state, and/or respiration, and/or body position, may be used to determine not only the level of therapy to deliver, but also the sampling frequency for the PPG and other sensors (e.g., used by the PPGSS). This data could also be used to place the device into a heightened state of readiness to treat a subject.

In one embodiment the detection of apnea and hyponea from a PPG/PPGSS can be converted into a rate or apnea hypopnea index (AHI) and the AHI can be used to determine an appropriate stimulation level (intensity, frequency, pulse width, duty cycle, bursting parameters etc.) for a treatment device under the control of the PPG/PPGSS. AHI can be measured again at the new stimulation level to determine if the new therapy paramater(s) provide adequate reduction of AHI. Depending on the result, stimulation could be further adjusted—upwards to further reduce AHI, or downwards to see if the first AHI rate returns (or if AHI increases at all), or the stimulation could be held at the first response level for a pre-determined amount of time or until there is a signal from the PPG/PPGSS that indicates it is likely safe to reduce the stimulation (e.g., based on a change in body position, sleep state, respiration effort or rate). In some aspects, systems designed to treat sleep apnea may comprise a separate device (e.g., a computer, laptop, or dedicated device such as an MDC 103) that is in communication with the PPG/PPGSS.

As shown by FIG. 3, a control algorithm for sleep-disordered breathing using a PPG or PPGSS device may comprise a five-step workflow. At step, 301, the PPG/PPGSS measures AHI using biomarker parameters obtained from the PPG and the one or more additional sensors (in the case of the PPGSS). The measured AHI is then evaluated using control logic at step 302 (Test condition 1). Potential test conditions include, e.g., an evaluation as to whether the AHI is increasing, above a threshold, above the least measured AHI, or whether the AHI is increasing at a rate above a predetermined threshold. If one or more of these conditions are true (or if a number above a predetermined threshold are true), the workflow may proceed to step 303, wherein the level of therapy is increased. Alternatively, if test condition 1 is evaluated and found not to be satisfied, the control logical ay proceed to a second test condition (Test condition 2, in this case). Potential test conditions include, e.g., an evaluation as to whether the AHI is decreasing, below a predetermined threshold, below the last measured AHI, or whether the rate of the AHI is decreasing. If one or more of these conditions are true (or if a number above a predetermined threshold are true), the workflow may proceed to step 305, wherein the level of therapy is decreased. Alternatively, if none are true the control logic may return to step 301, beginning another analysis cycle. Similarly, after steps 303 and 305 the control logic again returns to step 301.

With respect to step 303, an increase in therapy may comprise, e.g., an adjustment of the amplitude, frequency, pulse width, duty cycle, or bursting, of electrical stimulation provided by an implantable pulse generator. Typically, the amperage and/or duty cycle increases. In the case of a PAP device, increased therapy may comprise an increase in pressure. In the case of a negative pressure device, increased therapy may comprise an increase in negative pressure and/or of the duration/cycle of the application of negative pressure. In all cases, the increased therapy may be subject to upper bounds or limited based on a projected wakefulness impact.

With respect to step 305, a decrease in therapy may comprise, an adjustment that results in a change opposite to the adjustments applied in the case of an increase in therapy (e.g., for a PAP device pressure would be decreased, rather than increased).

To be clear, FIG. 3 represents a non-limiting example of an algorithm for adjusting a level of treatment provided by a treatment device in response to biomarker parameter data obtained from a PPG/PPGSS, in the context of a treatment for sleep apnea. In practice a control algorithm may utilize any combination of these steps, in any order, as well as additional test conditions.

FIG. 4 illustrates aspects of an exemplary algorithm for a PPGSS-based probability determination to trigger therapy or heightened system readiness for sleep-disordered breathing (SDB). At step 401, the PPGSS may determine a probability of sleep-deprived breathing onset or worsening ($P_1$). This probability may in turn be evaluated using one or more test conditions (e.g., Test condition 1, in this example) at step 402. If the test condition(s) are satisfied, the PPGSS may be configured to actuate a trigger or shift into a different mode (e.g., a higher-intensity treatment mode) at step 403. As shown by this figure, the PPG/PPGSS may be configured to optionally reevaluate $P_1$ after the mode shift (e.g., after a predetermined amount of time has elapsed).

Various factors related to SDB may be used as test conditions. For example, test conditions may evaluate one or more of the following biomarker parameters obtained from the PPG/PPGSS: body position, activity, sleep stage, AHI or change in AHI, respiratory parameter(s), heart rate, blood pressure, blood alcohol level, medications, and/or use of an opioid or sleep aid. In some aspects, a derived biomarker parameter may be evaluated (e.g., a metric obtained by processing a directly-detected or measured biomarker parameter). In some aspects, a test condition may include an algorithm that uses inter- or intra-patient historical data for one or more biomarker parameters. Exemplary test conditions include an evaluation as to whether: $P1>0$, $P_1>t_1$, $P_{1n}>P_{1n-x}$ (where $x=1, 2, 3, 4, \ldots, t_1$=a threshold).

The mode shift may comprise a switch to a different algorithm for processing the biomarker parameter data obtained by the PPG/PPGSS, and/or an increase in PPG/PPGSS sampling rate. In some aspects, the mode shift may comprise a change in the sensor(s) used to collect biomarker parameter data. For example, if SDB onset/worsening is predicted, the PPG/PPGSS may switch to more sensitive sensors, optionally at a higher sampling rate.

Figure 5:
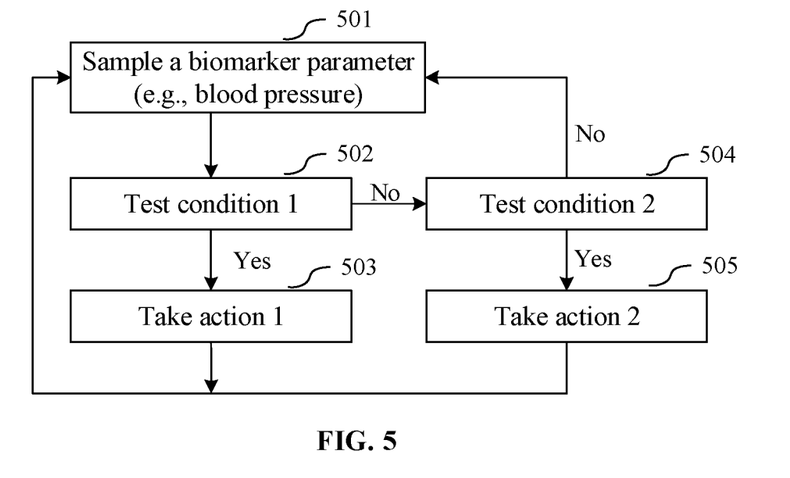
FIG. 5 is a flowchart illustrating aspects of an exemplary embodiment of a control algorithm used to control a PPGSS-based system for treating a condition.

FIG. 5 is a flowchart illustrating aspects of another exemplary embodiment of a control algorithm used to control a PPGSS-based system for treating a cardiac condition (e.g., for use by the PPG/PPGSS shown in FIG. 1). In this example, the PPG/PPGSS is configured to sample a biomarker parameter, e.g., blood pressure, at step 501. The sampled biomarker parameters are then evaluated based on test condition 1 at step 502. If the test condition is satisfied, the PPG/PPGSS may be configured to take action at step 503. Alternatively, the control logic may proceed to one or more additional test conditions (e.g., Test condition 2, step 504), each with additional associated actions (e.g., resulting in specific actions, as in step 505). The test conditions may comprise an evaluation as to whether the given biomarker parameter is above/below a threshold, above/below a prior recorded level, or increasing/decreasing above/below a pre-determined threshold. For example, in this case, the PPG/PPGSS may be configured to provide an audible or visual alert, to start (or stop) a therapy, or to increase, decrease, titrate or adjust a therapy. For example, if this algorithm is considered in the context of a system for treating cardiac conditions as shown in FIG. 1, the action performed at step 503 may comprise an increase in the pump flow rate if the tested biomarker parameter (e.g., blood pressure) is found to exceed a predetermined threshold at step 502.

Figure 6:
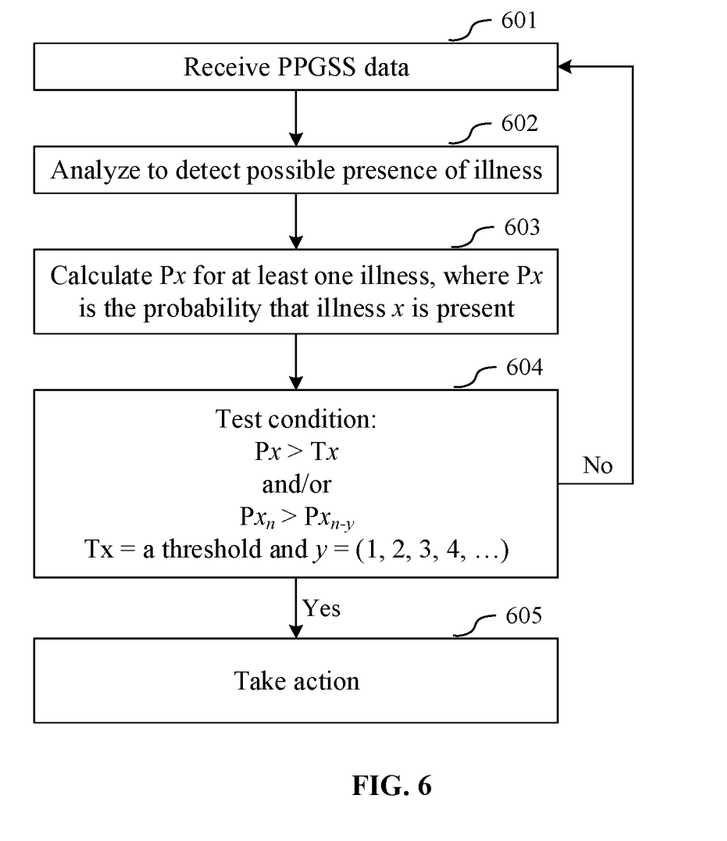
FIG. 6 is a flowchart illustrating aspects of an exemplary embodiment of a method for treating a human subject based on data collected using a PPGSS system described herein.

FIG. 6 is a flowchart illustrating aspects of an exemplary embodiment of a method for treating a human subject based on data collected using a PPGSS system described herein (e.g., using the cloud-based system depicted by FIG. 2).

As shown by this exemplary algorithm, PPGSS data for one or more biomarker parameters may be received (601) and analyzed (602) to detect the presence of illness (e.g., comorbidity). As part of this analysis, a probability ($P_x$) may be calculated for each illness that might be present (603). The analysis may be performed locally by the PPGSS or by a third party (e.g., a cloud-based service and/or a remote HCP). Moreover, the analysis may comprise the application of one or more artificial intelligence or machine learning algorithms. Px may be evaluated using one or more test conditions (604) and if it is found that a comorbid illness is present treatment may be applied or adjusted (605), as described elsewhere herein.

PPG and PPGSS for Treatment of Other Medical Conditions

The foregoing examples have illustrated the use of PPG and PPGSS embodiments in the context of treatments for sleep apnea and heart-related diseases/disorders such as arrhythmia or hypertension. However, the concept of using PPG alone or PPGSS to monitor a vital sign or bio marker, or an imputed parameter, and to optionally use the monitored parameter(s) as feedback to continuously, or semi-continuously, or periodically modulate therapy delivery in order to impact one or more metrics indicative of a medical condition can be applied broadly to any number of devices that can be used to deliver therapy for any number of conditions. In some aspects, PPG or PPGSS monitoring and feedback may be used to modulate medication doses, including pills, injectables, and inhalables. Some examples of the latter would include radiation, chemotherapy, external neuromodulation, ultrasound therapy, TENS, and many others. Moreover, in some aspects, the PPG or PPGSS monitoring can provide feedback that can be used to guide the application of treatment by an HCP rather than a treatment device.

By way of example, an element, or any portion of an element, or any combination of elements described herein may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A system for delivering therapy to treat a medical condition of a human subject, comprising:
    a photoplethysmography ("PPG") sensor configured to detect, measure, and/or monitor a first biomarker parameter of the subject, wherein the first biomarker parameter comprises data indicative of one or more of an oxygen saturation level, a heart rate, a respiration rate, a stroke volume, a cardiac output, a pulse pressure, a systemic vascular resistance, an arterial pressure, or a cardiac index, of the human subject;
    at least one additional sensor configured to detect, measure, and/or monitor one or more secondary biomarker parameters of the subject, wherein the secondary biomarker parameters comprise data indicative of a body temperature, an activity and/or body position, a presence or level of sweat on skin, or a single-electrode or low electrode count electrocardiogram ("ECG"), of the human subject; and
    a treatment device comprising a stimulator configured to administer electrical stimulation to at least one nerve of the human subject associated with upper airway patency, and a controller configured to control the stimulator;
    wherein the controller is further configured to
        determine an apnea-hypopnea index ("AHI"), body position, and sleep stage of the human subject based on the first biomarker parameter and the secondary biomarker parameters,
        determine whether the human subject is experiencing an onset or worsening of sleep-disordered breathing ("SDB") based on the determined AHI, body position, and sleep stage of the human subject, or a change in the determined AHI, body position, and/or sleep stage of the human subject compared to historical data, and
        cause the stimulator to switch to a higher-intensity treatment mode in response to determining that the subject is experiencing an onset or worsening of SDB.

2. The system of claim 1, wherein the first biomarker parameter comprises one or more of: an oxygen saturation level, a heart rate, a respiration rate, a cardiac output, a pulse pressure, a systemic vascular resistance, an arterial pressure, and/or a cardiac index, of the human subject.

3. The system of claim 1, wherein the secondary biomarker parameters comprise data indicative of a body temperature, a body position, and a presence or level of sweat on the skin, of the human subject.

4. The system of claim 1, wherein controller of the treatment device is further configured to
    determine an AHI, body position, and sleep stage of the human subject based on the first biomarker parameter and the secondary biomarker parameters, at a predetermined time point or after a predetermined time period has elapsed, after causing the stimulator to switch to a higher-intensity treatment mode;
    determine whether the subject is experiencing SDB at the predetermined time point or after the predetermined time period has elapsed; and
    cause the stimulator to switch to a lower-intensity treatment mode in response to determining that the human subject's SDB has ceased or is at a reduced level compared to a preceding determination.

5. The system of claim 4, wherein the switch to the lower-intensity treatment mode comprises a gradual titration of an amplitude, frequency, pulse width, duty cycle, and/or bursting parameters of the electrical stimulation.

6. The system of claim 1, wherein the treatment device is a medical device implanted in the subject.

7. The system of claim 1, wherein the switch to the higher-intensity treatment mode comprises a gradual titration of an amplitude, frequency, pulse width, duty cycle, and/or bursting parameters of the electrical stimulation.

8. The system of claim 1, wherein the treatment device is an external stimulation device.

9. The system of claim 7, wherein the treatment device is further configured to stimulate the human subject's heart.

10. The system of claim 7, wherein the treatment device is configured to stimulate:
    a) at least one nerve of the human subject, optionally one or more of a vagus, phrenic, sacral, tibial, hypoglossal, pharyngeal, glossopharyngeal, occipital, spinal, cranial, cavernous, facial, radial, ulnar, auditory, esophageal, laryngeal, femoral, frontal, cardiac, cervical, hypogastric, plantar, mandibular, perineal, pelvic, saphenous, splanchnic, splenic, tympanic, renal, thoracic, vestibular or trigeminal nerve of the human subject, or any of their branches; and/or
    b) at least one tissue or organ of the human subject, optionally one or more of the heart, carotid sinus, vocal cords, tongue, or muscles, of the human subject.

11. The system of claim 1, wherein the treatment device is configured to stimulate the hypoglossal nerve and/or the phrenic nerve of the human subject.

12. The system of claim 1, wherein the controller is further configured to determine whether the human subject is experiencing an onset or worsening of SDB based on determining that the human subject's AHI is above a preset threshold, or increasing at a rate above a preset threshold.

13. The system of claim 1, wherein the controller of the treatment device is further configured to cause the PPG sensor, and/or the at least one additional sensor, to increase a sampling rate after determining that the human subject is experiencing an onset or worsening of SDB.

14. The system of claim 12, wherein the treatment device is configured to:
    a) provide electrical stimulation; and
    b) adjust one or more parameters of the electrical stimulation based on the first biomarker parameter, wherein adjustment comprises modulation of the amplitude, frequency, pulse width, duty cycle, or bursting parameters of the electrical stimulation.

15. The system of claim 12, wherein the treatment device is configured to
    a) provide electrical stimulation to at least one nerve associated with upper airway patency; and
    b) adjust one or more parameters of the electrical stimulation based on the first biomarker parameter and/or the second biomarker parameter, wherein adjustment comprises modulation of the amplitude, frequency, pulse width, duty cycle, or bursting parameters of the electrical stimulation.

16. The system of claim 1, wherein the system further comprises a positive air pressure ("PAP") device and the controller is further configured to cause the PAP device to increase a pressure level of air administered to the subject in response to determining that the subject is experiencing an onset or worsening of SDB.

17. The system of claim 1, wherein the system further comprises a negative air pressure device and the controller is further configured to cause the negative air device to increase a negative pressure level, and/or a duration of the application of negative pressure administered to the subject, in response to determining that the subject is experiencing an onset or worsening of SDB.

18. A method for treating a medical condition of a human subject, comprising:
    detecting and/or monitoring, by a photoplethysmography ("PPG") sensor, a first biomarker parameter of the subject, wherein the first biomarker parameter comprises one or more of an oxygen saturation level, a heart rate, a respiration rate, a stroke volume, a cardiac output, a pulse pressure, a systemic vascular resistance, an arterial pressure, or a cardiac index, of the human subject;
    detecting and/or monitoring, by at least one additional sensor, one or more secondary biomarker parameters of the human subject;
    determining an apnea-hypopnea index ("AHI"), body position, and sleep stage of the human subject based on the first biomarker parameter and the secondary biomarker parameters;
    determining whether the human subject is experiencing an onset or worsening of sleep-disordered breathing ("SDB") based on the determined AHI, body position, and sleep stage of the human subject, or a change in the determined AHI, body position, and/or sleep stage of the human subject compared to historical data;
    causing a treatment device to administer a higher-intensity treatment of electrical stimulation to at least one nerve associated with upper airway patency of the human subject after determining that the subject is experiencing an onset or worsening of SDB.

19. The method of claim 18, wherein the medical condition comprises: sleep apnea, hypertension, or an abnormal heart rhythm/rate.

20. The method of claim 18, wherein the treatment device comprises:
    a) an implantable pulse generator connected to one or more electrodes, or
    b) an external stimulator.

* * * * *